United States Patent
Yampolsky et al.

(10) Patent No.: US 9,133,220 B2
(45) Date of Patent: Sep. 15, 2015

(54) BORON-CONTAINING 5-ARYLIDENE-3,5-DIHYDRO-4H-IMIDAZOL-4-ONES

(75) Inventors: Ilia Victorovich Yampolsky, Moscow (RU); Konstantin Anatolyevich Lukyanov, Moscow (RU); Mikhail Sergeyevich Baranov, Moscow (RU)

(73) Assignee: Evrogen Joint Stock Company, Moscow (RU)

( * ) Notice: Subject to any disclaimer, the term of this patent is extended or adjusted under 35 U.S.C. 154(b) by 0 days.

(21) Appl. No.: 14/417,934

(22) PCT Filed: Aug. 20, 2012

(86) PCT No.: PCT/RU2012/000682
§ 371 (c)(1),
(2), (4) Date: Jan. 28, 2015

(87) PCT Pub. No.: WO2014/031021
PCT Pub. Date: Feb. 27, 2014

(65) Prior Publication Data
US 2015/0177254 A1  Jun. 25, 2015

(51) Int. Cl.
*C07F 5/02* (2006.01)
*G01N 33/58* (2006.01)

(52) U.S. Cl.
CPC . *C07F 5/027* (2013.01); *C07F 5/02* (2013.01); *G01N 33/582* (2013.01)

(58) Field of Classification Search
CPC .................................................. C07F 5/027
See application file for complete search history.

(56) References Cited

PUBLICATIONS

Baranov et al. "Conformationally Locked Chromophores as Models of Excited-State Proton Transfer in Fluorescent Proteins" Journal of the American Chemical Society, 2012, vol. 134, pp. 6025-6032.*
Baranov et al., Conformationally Locked Chromophores as Models of Excited-State Proton Transfer in Fluorescent Proteins, J Am Chem Soc (2012), 134(13):6025-6032.
Lippincott-Schwartz et al., Development and use of fluorescent protein markers in living cells, Science (2003), 300(5616):87-91.
Baranov et al., Red-shifted fluorescent aminated derivatives of a conformationally locked GFP chromophore, Chemistry (2014), 20(41):13234-13241.
Frizler et al., Chemical introduction of the green fluorescence: imaging of cysteine cathepsins by an irreversibly locked GFP fluorophore, Org Biomol Chem (2013), 11(35):5913-5921.

* cited by examiner

*Primary Examiner* — Joseph Kosack
(74) *Attorney, Agent, or Firm* — Bret E. Field; Bozicevic, Field & Francis LLP

(57) ABSTRACT

Novel compounds of the general formula

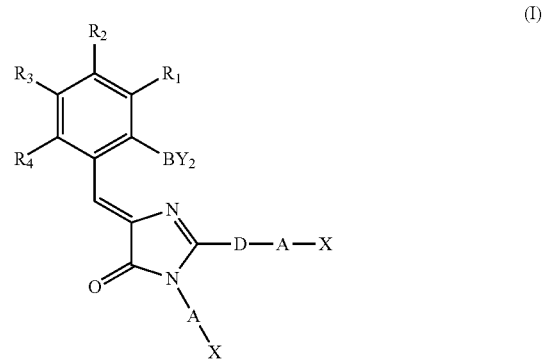

are introduced, containing 5-arylidene-3,5-dihydro-4h-imidazol-4-one core. These compounds can be used for fluorescent staining of cell membranes, biomolecules' labeling in vivo and in vitro, a number of compounds also have photoacidic properties. This allows to use them, for example, as instruments to drastically change pH of a medium, and also as dynamic fluorescent probes for investigation of complex objects like proteins and micellae, as well as in studies of hydration dynamics and in photolithography.

6 Claims, No Drawings

BORON-CONTAINING 5-ARYLIDENE-3,5-DIHYDRO-4H-IMIDAZOL-4-ONES

FIELD OF THE INVENTION

Novel compounds of general formula

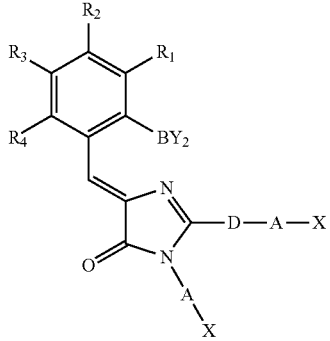

are proposed, which contain a 5-arylidene-3,5-dihydro-4H-imidazol-4-one nucleus and can be used for fluorescent labeling of subcellular structures and biomolecules in vivo and in vitro. The compounds also have photoacidic properties which make them suitable for use, for example, as instruments for drastically changing the pH of a medium, or as dynamic fluorescent probes for examining complex objects, in particular proteins and micellae, as well as in dynamic hydration studies and for photolithography.

BACKGROUND OF THE INVENTION

The fast development of the fluorescent microscopy techniques over the last years has made it possible to visualize many biological processes. Among the most important tools used both in biomedical tests and in scientific research are fluorescent dyes allowing to observe target molecules and media in a real-time mode.

Various fluorescent dyes have been used in scientific research for a long time, however the necessity of developing novel fluorescent stain reagents has arisen with the appearance of fluorescent microscopy.

The use of living systems imposed many additional restrictions on the structure of such markers. These compounds must be hydrophilic enough (to exclude non-specific hydrophobic interactions), their absorbance and emission spectra have to lie in visible or even more red region (to reduce phototoxicity and background autofluorescence), and the molecular weight has to be as low as possible (to minimize the influence on labeled biomolecules).

These criteria have significantly limited the range of dyes used, and also narrowed the areas of their application.

This stimulated researchers to develop new specific compounds, which lack such limitations.

Thus, the new dyes with different structures for use in cell biology were created—derivatives of coumarin, rhodamine, carbopyronine and oxazine, available for example from ATTO-TEC [Catalogue 2009/2010 p. 16]. The dyes from Alexa trademark have similar properties. These compounds have high photostability, but their molecular mass is big enough, which limits their application.

The dyes with dipyrrilmethene structure have the structure, similar to the proposed invention [A. Schmitt, B. Hinkeldey, M. Wild, G. Jung, *J. Fluoresc.*, 19, 755 (2009)], [K. Tram, H. Yan, H. A. Jenkins, S. Vassiliev, D. Bruce, *Dyes and Pigments* 82(3), 392 (2009)]:

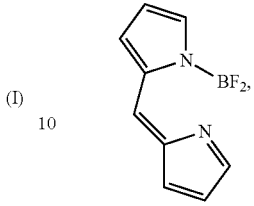

with fluoroborylic group in the chromophore nucleus.

Another structural analogue is a dye with structural formula:

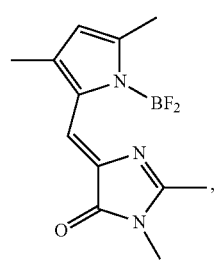

(Z)-4-((1-(difluoroboryl)-1H-pyrrol-2-yl)methylene)-1H-imidazole-5(4H)-one, developed by Burgess group [L. Wu, K. Burgess, *J. Am. Chem. Soc.*, 130(12), 4089 (2008)], also containing fluoroborylic group in the chromophore nucleus.

However the above mentioned dyes are rather expensive and synthetically difficult to obtain. This is why they are expensive at the moment.

The chromophore of the Green Fluorescent Protein family (GFP, natural protein from *Aequorea victoria* jellyfish (avGFP)), is close to the structure of proposed fluorescent dye:

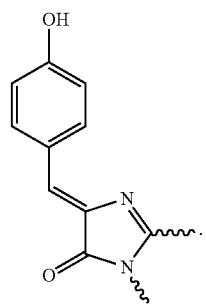

This chromophore is responsible for fluorescence in these proteins after irradiation with light of proper wavelength, but it is not fluorescent in the solution itself, if obtained by chemical synthesis or extracted from the protein. The change in its properties is due to the interaction between two or more amino acid residues, after autocatalytic formation of the chromophore, and their protein surrounding. [J. L. Schwartz, G. H. Petterson, *Science*, 300, 87 (2003)], [D. M. Chudakov, M. V. Matz, S. Lukyanov, K. A. Lukyanov, *Physiol Rev.*, 90(3), 1103 (2010)].

The artificially synthesized GFP chromophore has the structure, closest to the proposed invention:

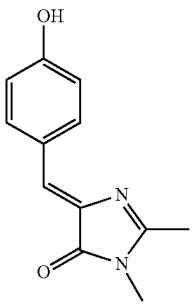

(Z)-4-(4-hydroxybenzylidene)-1,2-dimethyl-1H-imidazole-5(4H)-one and its fluorinated derivatives. These compounds do not show any fluorescent properties in solution, but gain them only after binding to the target molecule, which locks chromophore conformationally due to complex space interactions, and therefore ensures the fluorescence [J. S. Paige, K. Y. Wu, S. R. Jaffrey, Science, 333, 642 (2011)]. These properties allow the application of this chromophore in limited list of specific tasks, only when the desired fixation of chromophore by target molecule takes place.

The variety of applied tasks, demanding the use of fluorescent dyes, requires search and development of very diverse compounds, different in the color of fluorescence and absorbance region, hydrophobic/hydrophilic properties, and with different substituents, ensuring their binding to certain targets.

The hypothesis that chemical compounds with the structure similar to GFP chromophore might become useful as low-weight fluorescent dyes, was at the basis of the proposed invention.

However until now there was no evidence of successful use of the GFP chromophore analogues in this role, as it is seen from the sources, cited above.

DISCLOSURE OF THE INVENTION

Inventors have found that introduction of boron-containing substituent into the arylidene nucleus of basic GFP chromophore structure allows the formation of an inner coordination boron-nitrogen bond and a required auto-fixation of the chromophore structure. This allows to obtain structures with high quantum yields of fluorescence, with different fluorescence excitation and emission peaks, including those lying in a red part of visible spectrum.

Present compounds may also contain carboxylic, azido and amino substituents for conjugation with biological targets.

DESCRIPTION OF THE PREFERRED EMBODIMENTS

The present invention provides the compounds with formula (I):

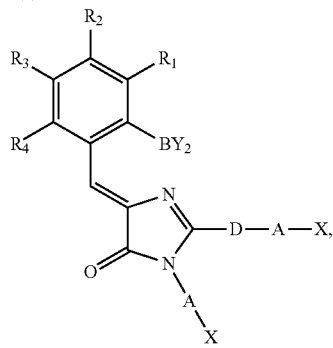

where

A is selected from hydrogen, linear or branched $C_{1-6}$ alkyl or $C_{4-6}$ cycloalkyl, D is selected from double or triple bond, aryl, heteroaryl, or may be absent, X is selected from hydrogen, halogen, unsubstituted or $C_{1-6}$ alkyl substituted aminogroup, in which substituents not necessarily form cyclic pyrrole or pyrrolidine derivatives, or $C_{4-6}$ cycloalkyl substituted amino group, azide, isothiocyanate, isocyanate, alcohol or thiol group, acetylene fragment, carboxylic group, or may be absent, Y are independently selected from fluorine, hydroxyl or alkoxyl group with $C_{1-6}$ alkyl substituent, $R_1$, $R_2$, $R_3$, $R_4$ are independently selected from hydrogen, halogen, unsubstituted or $C_{1-6}$ alkyl substituted aminogroup, in which substituents not necessarily form cyclic substituted pyrrole or pyrrolidine derivatives, or $C_{4-6}$ cycloalkyl substituted amino group, hydroxyl or $C_{1-6}$ alkyl alkoxyl group, and also its salts and/or stereoisomers and/or their conjugates.

The compounds referenced above have fluorescent properties. They can be used as fluorescent dyes for labeling the biomoleculeslabeling or cellular structures.

The preferable example of the invention is the compound (Z)-4-(2-(difluoroboryl)-4-hydoxybenzylidene)-1,2-dimethyl-1H-imidazole-5(4H)-one, which shows optimal properties for biomolecules labeling, for example, high solubility in water and the highest quantum yield of fluorescence in water.

The preferable example of the invention is also the compound (Z)-4-(4-(diethylamino)-2-(difluoroboryl)benzylidene)-1,2-dimethyl-1H-imidazole-5(4H)-one, which is suitable for staining the cell structures, cell membranes in particular, due to its high hydrophobicity and the highest quantum yield of fluorescence in non-polar solvents.

Another preferable example is the compounds of formula (I), where $R_2$ is OH group, demonstrating photoacidic properties.

The compound (Z)-4-(2-(difluoroboryl)-3,5-difluoro-4-hydroxybenzylidene)-1,2-dimethyl-1H-imidazole-5(4H)-one shows very strong photoacidic properties, as pKa of its excited state (upon excitation with visible light) lies in the negative region, which allows to attribute this compound to "super" photoacids [L. M. Tolbert, K. M. Solntsev, Acc. Chem. Res., 35, 19 (2002)].

According to the invention, new compounds can be obtained according to the scheme 1 below ($X=R_1$, $R_2$, $R_3$, $R_4$). Exact methods of their synthesis are described in Examples 1-5.

Scheme 1

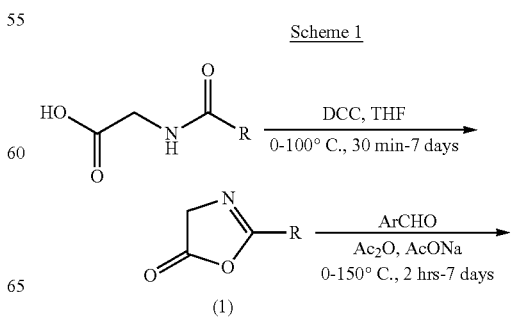

(1)

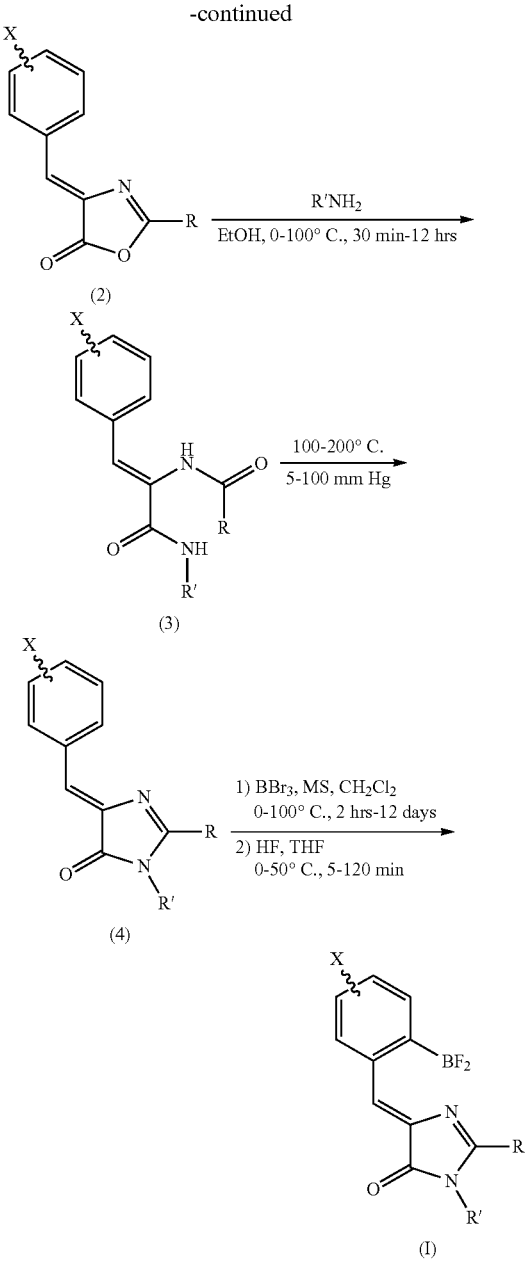

Substituted arylidene-1H-imidazole-5(4H)-ones (4) are the key intermediates in the synthesis of the proposed dyes. There exist many ways to obtain these compounds, including condensation of 1H-imidazole-5(H)-ones with aromatic compounds, [O. Shimomura, *FEBS Lett.* 104, 220 (1979)], [A. Baldridge, K. M. Solntsev, C. Song, N. Tanioka, J. Kowalik, L. M. Tolbert, *Chem. Comm.* 46, 5686 (2010)], cycloaddition of imidates to aldimines [J. M. Lerestif, J. P. Bazureau, J. Hamelin, *Tetrahedron. Lett.,* 49, 4639 (1993)] or use of 2-azido cinnamic acids [P. M. Fresneda, P. Molina, M. A. Sanz, *Synlett.,* 8, 1190 (2000)]. Among these methods the cyclization of amides of N-acelydehydroaminoacids (3) is the most effective. Such compounds can also be obtained in different ways [A. B. Hughes "Amino Acids, Peptides and Proteins in Organic Chemistry", Weinheim; Wiley-VCH Verlag GmbH & Co. KGaA, 1, (2009)], [C. Bonauer, N. Walenzyk, B. König, *Synthesis,* 1, 1 (2006)], [U. Schmidt, A. Lieberknecht, J. Wild, *Synthesis,* 3, 159 (1988)], among which the aminolysis of various arylidene-1H-oxazole-5(4H)-ones (2) is the most successful [S. S. Alkaabi, A. S. Shawal, *Can. J. Chem.,* 10, 2515 (1992)]. The methods to synthesize compounds (2) are quite diverse [C. D. Palmer "The Chemistry of Heterocyclic Compounds, Volume 60: Oxazoles: Synthesis, Reactions, and Spectroscopy" Weinheim; Wiley-VCH Verlag GmbH & Co. KGaA. (2004)], but the key one is the condensation of carbonyl compounds with cyclic derivatives of N-acylglycine (1). These can be obtained from corresponding N-acylglycines with the help of various dehydrating agents [C. D. Palmer "The Chemistry of Heterocyclic Compounds, Volume 60: Oxazoles: Synthesis, Reactions, and Spectroscopy" Weinheim; Wiley-VCH Verlag GmbH & Co. KGaA. (2004)].

Standard method of synthesis of compounds I according to the proposed invention is described in the scheme 1. The first step is a dehydration of N-acylglycine derivatives using dicyclohexylcarbodiimide (DCC) [D. Cabaret, J. Liu, M. Waksel-man, *Synthesis,* 5, 480 (1994)]. This reaction is carried out in different solvents, but tetrahydrofurane (THF) is the most convenient; the conditions and reaction times may vary in a wide range as indicated in the scheme. Next step is a condensation of compounds (1) with equivalent amounts of various aromatic aldehydes (ArCHO). The most convenient procedure for this condensation is the use of acetic anhydride ($Ac_2O$) in the presence of equivalent amount of sodium acetate (AcONa) [E. J. Erlenmeyer, *Jestus Lieb. Ann. der Chem.* 275. 1 (1893)]. Necessary temperature and time for this reaction depend on the structure of aromatic aldehydes and settle in the range, indicated in the scheme. Aminolysis of compounds (2) proceeds under action of different primary amines ($R'NH_2$) in various inert solvents, among which ethanol (EtOH) is the most useful. The conditions for this reaction also depend on the structure of amine and substrate (2), and may be changed in the range, described in the scheme. Further dehydration of compounds (3) can be performed by dehydrating agents in different solvents, but the most convenient method is a thermic dehydration under reduced pressure [C. Granacher, G. Gulbas, *Helvetica chemical acta.,* 10, 819 (1975)]. The conditions of the process are greatly dependent on the character of substituent R' and can vary in the range, presented on the scheme.

If reactive substituents are present in the target structure, protective groups should be introduced at this step, a comprehensive list of which is shown in the Greene's manual along with the methods of their introduction and cleavage [T. W. Greene, *"Protective Groups in Organic Synthesis"*, John Wiley & Sons, New York, (1981)].

The key step of the synthesis of compounds I according to the proposed invention is borylation of 5-arylidene-3,5-dihydro-4-H-imidazole-4-ones (4). This reaction is performed under the action of excess amounts of boron tribromide [N. Ishida, T. Moriya, T. Goya, M. J. Murakami, *J. Org. Chem.,* 75, 8709 (2010)]. The reaction is performed in the presence of molecular sieves (MS) which absorb hydrobromic acid, in different inert solvents, among which dichloromethane is the most convenient [M. S. Baranov, K. A. Lukyanov, A. O. Borissova, J. Shamir, D. Kosenkov, L. V. Slipchenko, L. M. Tolbert, I. V. Yampolsky, K. M. Solntsev, *J. Am. Chem. Soc.,* 134, 6025 (2012)]. The reaction conditions depend on the substrate's structure and may vary in the range indicated in the scheme. Further exchange of bromine atoms in dibromoboryl group to fluorine atoms is performed under the action of HF solutions in various solvents, the most useful is tetrahydrofurane. This reaction is rather fast, and may be carried out in conditions, shown in the scheme.

Further modification of these compounds may include different organic reactions, which will not affect difluoroboryl substituent and arylidene-1H-imidazole-5(4H)-one core. Among these modifications are introduction and cleavage of different protective groups, ester hydrolysis, nucleophilic substitution of halogen atoms, amide, ether and ester synthesis, condensations with carbonyl compounds and dehydration. Some examples of these transformations are shown in Examples 1-5.

Characteristics of main properties of novel compounds, such as spectral characteristics, solubility in water and toxicity, are shown in Examples 6-9.

DEFINITIONS

Compounds I of the present invention may contain asymmetric centers, chiral axes and chiral planes (as described in the manual—[E. L. Eliel, S. H. Wilen, "*Stereochemistry of Carbon Compounds*", John Wiley & Sons, New York, 1119 (1994)]) and may be present as racemic mixtures or as individual isomers, as well as various mixtures with all possible combinations of these isomers. In addition, the described compounds may be present as tautomers, and both tautomeric forms are included in the present invention, even if there is only one tautomeric form described. For example, any reference to the compound A, given below, should be understood as including its tautomeric form B, and vice versa, and their mixture as well.

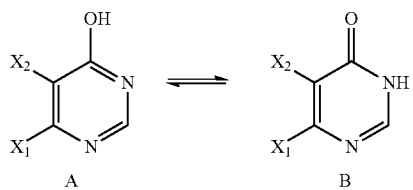

In the case when any variable (for example, $R^1$, $R^2$, $R^3$, A, D etc.) is found more than once in any substituent, its definition in every case doesn't depend on any other case of utilization. Besides, the combination of substituents in variables is possible only in case if the obtained compounds are stable.

A substituent is an atom or a group of atoms, substituting hydrogen atom in a primary structure.

A reactive substituent is a substituent capable to react with other chemical compounds or groups.

It should be understood, that according to the proposed invention substituents and a character of substitution in compounds may be chosen by an expert in the current field for obtaining compounds, which will be chemically stable and can be easily synthesized from available materials upon known procedures, and also the procedures described below. It should be understood that if a substituent itself possesses more than one substituent, then the indicated substituents may be present at the same carbon atom or at different atoms, only if the structure formed is stable. The term "not necessarily substituted by one or more substituents" should be understood as equal to the term "not necessarily substituted, at least, by one substituent", the most preferable is the case when zero to three substituents are present.

In the context of present description the term "alkyl" includes linear and branched saturated aliphatic hydrocarbonic groups, containing from one to ten carbon atoms, if nothing else is indicated. For example, $C_1$-$C_{10}$ with reference to "$C_1$-$C_{10}$ alkyl" is determined as a group, including 1, 2, 3, 4, 5, 6, 7, 8, 9 or 10 carbon atoms in linear, branched or cyclic variant of organization. For example, the term "$C_1$-$C_{10}$ alkyl" includes exactly methyl, ethyl, propyl, butyl, pentyl, hexyl, heptyl, octyl, nonyl, decyl etc.

The term "cycloakyl" or "carbocycle" means cyclic rings of alkanes, containing from three to eight carbon atoms, if nothing else is indicated, or any other number in the current range (for example, it can be cyclopropyl, cyclobutyl, cyclopentyl, cyclohexyl, cycloheptyl or cyclooctyl).

In some cases the substituents can be determined as an interval of carbon atoms, which includes zero case, for example, ($C_0$-$C_6$) alkylene-aryl. If aryl is combined with phenyl, then the specified definition may include phenyl itself along with —$CH_2Ph$, —$CH_2CH_2Ph$, —$CH(CH_3)$, —$CH_2CH(CH_3)Ph$ etc.

In the context of the current description, the term "aryl" means any stable monocyclic or carbocyclic carbon-containing ring, including up to 12 atoms in every ring, where at least one of the rings is aromatic. Examples of such aryl element include phenyl, naphtyl, tetrohydronaphtyl, indanyl, biphenyl, phenantryl, antryl and acenaphtyl. In case when aryl substituent is bicyclic and one ring is not aromatic, it should be understood that attachment is via aromatic ring.

In the context of current description, the term "heteroaryl" means a stable monocyclic, bicyclic or tricyclic ring, containing up to 10 atoms in each ring, where at least one ring is aromatic and contains from 1 to 4 heteroatoms—O, N and/or S. According to this definition heteroarylic groups include, without any restrictions, benzoimidazolyl, benzofuranyl, benzofyrazanyl, benzopyrazolyl, benzotriazolyl, benzothiophenyl, benzoxazolyl, carbazolyl, carbolinyl, cynnolinyl, furanyl, indolinyl, indolyl, indolazinyl, indazolyl, isobenzofuranyl, isoindolyl, isoquinolyl, isothiazolyl, isoxazolyl, naphtpyridinyl, oxadizolyl, oxazolyl, isoxazolyl, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzyl, benzothiazolyl, benzothienyl, quinolinyl, isoquinolinyl, oxazolyl and tetrahydroquinolyl. In the case when heteroaryl substituent is bicyclic, one ring is not aromatic or doesn't contain heteroatoms, it should be understood that attachment is via aromatic ring or the ring with heteroatom respectively. If heteroaryl contains a nitrogen atom, then corresponding N-oxides are also included into the current definition.

The terms "halo" and "halogen", which are used in the current description, include chlorine, fluorine, bromine and iodine, which is obvious for experts in this filed. The term "keto" means "carbonyl" (C═O).

The present invention also provides protected compounds of the formula I. For example, if the compounds of formula I contain groups, such as hydroxyl, carboxy, thio, or any other group, containing one or more nitrogen atoms, then the above indicated groups can be protected with the appropriate protective groups. Comprehensive list of suitable protective groups is described in Greene's manual [T. W. Greene, "*Protective Groups in Organic Synthesis*", John Wiley & Sons, New York, (1981)], the description of this manual is included in the present claim as a reference. Protected derivatives of compounds with the formula I can be obtained by known procedures.

According to the present invention, salts of compounds include salts, derived from inorganic acids, such a hydrochloric, hydrobromic, sulphuric, sulphaminic, phosphoric, nitric etc., as well as salts on the base of organic acids, such as acetic, propionic, succinic, glycolic, stearic, lactic, malic, tartaric, citric, ascorbic, maleic, phenylacetic, glutamic, benzoic, salicylic, sulphanylic, fumaric, toluenesulfonic, methanesulfonic, ethanedisulfonic, oxalic, trufluoroacetic etc.

The pKa value* is understood as a negative decimal logarithm of the constant of dissociation of an acid. The constant of dissociation of an acid is an equilibrium constant of a reaction of dissociation of an acid on hydrogen ion and an acid residue's anion.

The pKa* value is defined as a value of pKa of an excited state of a molecule.

Excited state is an energy state of a molecule and other quantum systems, characterized by exceeding energy in comparison to the ground state. In the current invention molecules become excited due to the absorbance of a quantum of light.

In the present invention, biomolecules are organic compounds, which can be produced by living organisms. Biomolecules include proteins, peptides, polysaccharides, nucleic acids, lipids, aminoacids, nucleotides, oligosaccharides, metabolites, hormones, neurotransmitters, vitamins.

Cell membranes are defined as functionally active surface structures, limiting cytoplasm and the majority of cell's organelles, they also form unified intracellular system of tubules, folds, closed regions. Membrane structures of cells are presented by surface membrane (cellular, or plasma membrane) and intracellular (subcellular) membrane. There are, for example, mitochondrial, nuclear, lysosomal membranes, membranes of canalicular apparatus of Golgi's apparatus, of endoplasmic reticulum, of sarcoplasmic reticulum etc.

Fluorescence is a physical process, a form of luminescence. Fluorescence is usually defined as a radiative transfer of the excited state from the lowest singlet oscilating level S1 to the ground state S0. In a general case fluorescence is defined as a spin allowed radiative transition between two states of the same multiplicity: either singlet levels S1-S0 triplet T1-T0. Typical lifetime of such excited state is $10^{-11}$-$10^{-6}$ s.

Fluorescence resonance energy transfer (inductive-resonance energy transfer, FRET) is a mechanism of energy transfer between two chromophores (from donor to acceptor), which takes place without photon emission and is a result of dipole-dipole interaction between donor and acceptor.

Photoacidity is an ability to dissociate with formation of $H^+$ ion under the action of visible light. Photoacidity is characterized by constants of acidity of ground and excited states. Förster's equation describes the relationship between acidity constants of ground and excited states and energy of transfer between the states.

Quantum yield is defined as a value, which shows the ratio between mean quantity of emitted quanta and one absorbed quantum.

Fluorescence lifetime is a value equal to the time interval from the absorption of a radiation quantum by a molecule and its transfer to the excited state until the following radiative transition to the ground state.

Bathochromic shift is a change in absorbance or emission spectrum, when the maximum band of the spectrum is shifted to a longer wavelength.

Hypsochromic shift is a change in absorbance or emission spectrum, when the maximum band of the spectrum is shifted to a shorter wavelength.

Spectral properties of a compound are defined as a set of emission and absorption spectra with the maximum bands and the value of quantum yield.

The absorption spectrum is a distribution of values of absorption intensities depending on wavelength of the absorbed radiation.

The emission spectrum is a distribution of values of emission intensities depending on wavelength for a given frequency of the exciting radiation.

The partition coefficient is defined as a value, equal to decimal logarithm of the ratio between equilibrium concentrations of a compound, dissolved in a two-phase system, consisting of two almost immiscible solvents.

All indicated temperature values are in Celsius scale, if nothing else is indicated.

Spectral Properties

Comprehensive description of spectral characteristics of several examples of compounds with the formula I is given below in the present document.

In whole, spectral characteristics of compounds of the formula I are similar to the corresponding synthetic chromophores of fluorescent proteins and their analogs based on 5-arylidene-3,5-dihydro-4H-imidazole-4-one. However, unlike the specified chromophores, compounds from the present invention possess greater values of quantum yields of fluorescence.

Moreover, the presence of $BF_2$-group leads to the shift of the spectra to red region of visible spectrum by 20-40 nm.

The compounds of the formula I, which have OH-group in $R_2$ position, can be found in two forms—protonated and deprotonated—depending on the pH of the solution, due to the presence of a phenol group with pKa 6.4. Deprotonated form is characterized with bathochromic shift in absorption and fluorescence spectra.

Emission and absorption spectra of p-HOBDI-BF2 ((Z)-4-(2-(difluoroboryl)-4-(hydroxybenylidene)-1,2-dimethyl-1H-imidazole-5(4H)-one) in different solvents are similar to the spectra of p-HOBDI ((Z)-4-(4-hydroxybenylidene)-1,2-dimethyl-1H-imidazole-5(4H)-one), but possess bathochromic shift by 30-40 nm (see Table 1). As cationic form of p-HOBDI-BF2 would not be fluorescent due to the bond break between boron and nitrogen, only anionic and neutral forms of chromophores are compared. However, the main distinction between p-HOBDI and p-HOBDI-BF2 is a dramatically increased fluorescence due to the inhibition of the rotation of phenol and imidazole rings because of the coordination between boron atom and nitrogen atom from imidazole ring. The value of a quantum yield of fluorescence in acetonitrile for p-HOBDI-BF2 is 0.73, and fluorescence lifetime is 3.2 ns. The indicated extremely high value of quantum yield of fluorescence is close to the quantum yield of fluorescence of green fluorescent protein wtGFP (0.79) and quantum yield of fluorescence of another boron-containing compound with rotation restriction, described by Wu and Burgess (0.81).

Hydrophilicity

Hydrophilicity is an important quality for the practical application of fluorescent dyes. Hydrophilicitycan be estimated by solubility in water, and also by partition coefficient water-octanol. Thus, the measured solubility in water for compounds p-HOBDI-BF2, F-p-HOBDI-BF2, di-F-p-HOBDI-BF2 is high in comparison with the majority of fluorescent dyes and is 1 µM at acidic and neutral values of pH. At weakly alkaline pH values the solubility increases many times (more than 10 fold), which is due to the transition of dyes into anionic state (phenol group dissociation). Partition coefficient water-octanol is another indicator, testifying high hydrophilicity of the obtained dyes with the formula I, where $R_1$, $R_2$, $R_3$, $R_4$ independently mean hydrogen, halogen, unsubstituted aminogroup or hydroxyl group. Values of this coefficient are more than 4 for three indicated examples (anionic form, pH 10).

Photoacidity

For compounds of the formula I, containing phenolic OH-group, high photoacidity—an ability to dissociate with formation of H$^+$ ion under the action of visible light—is a distinctive feature. Photoacidity is characterized by acidity constants of ground and excited states.

p-HOBDI-BF2 pKa=6.4, pKa*=2 diF-p-HOBDI-BF2($^1$) pKa=5.2, pKa*<0.

($^1$)((Z)-4-(2-(difluoroboryl)-3,5-difluoro-4-hydroxybenzylidene)-1,2-dimethyl-1H-imidazole-5(4H)-one)

Absolute pKa values for p-HOBDI-BF2 are close to the corresponding values for orto- and para-cyanophenols [S. G. Schulman, W. R. Vincent, W. J. M. Underberg, *J. Phys. Chem.*, 85, 4068 (1981)], and the difference between pKa of excited and ground states is in the range of typical values for substituted phenols [Z. Rappoport, "The Chemistry of Phenols", John Wiley & Sons, New York, Ch 7, (2003)] and corresponds to the values in "normal" photoacids.

Meanwhile for diF-p-HOBDI-BF2 absolute values of pKa of ground and excited states are close to the parameters of different complexly substituted polyaromatic structures, such as, for example, 8-hydroxy-1,3,6-tris(N,N-dimethylsulfonamido)pyrene [Z. Rappoport, "The Chemistry of Phenols", John Wiley & Sons, New York, Ch 7, (2003)]. At the same time, the difference between pKa values is several points more, then in p-HOBDI-BF2, and pKa of excited state is in the range of negative values, which allows to indicate this compound as a "super" acid [L. M. Tolbert, K. M. Solntsev, *Acc. Chem. Res.*, 35, 19 (2002)]. Similar compounds have a significant effect of excited state proton transfer, which allows to use them as instruments for rapid pH change [J. H. Clark, S. L. Shapiro, A. J. Campillo, K. R. Winn, *J. Am. Chem. Soc.*, 101, 746 (1979)], as dynamic fluorescent probes for investigations of complex objects, such as proteins [M. R. Loken, J. W. Hayes, J. R. Gohlke, L. Brand, *Biochem.*, 11, 4779 (1972)] and micellae [M. Gutman, E. Nachliel, D. Huppert, *Eur. J. Biochem.*, 125, 175 (1982)], in studies of hydration dynamics [D. Huppert, E. Kolodney, *Cheer. Phys.* 63, 401 (1981)] and for photolithography [E. S. Mansueto, C. A. Wight, *J. Am. Chem. Soc.* 111, 1900 (1989)].

At the same time, unlike the majority of described photoacids, these compounds have absorption and fluorescence peaks in visible range, which allows to apply them in media, that are not transparent for ultraviolet radiation.

Toxicity

Low toxicity is a necessary property for the compounds from the invention for their utilization as fluorescent dyes for biomolecules labeling in vivo. The compounds from the invention do not have any toxic effect on mammalian cells in high concentrations (up to 10 µM) and do not prevent their growth in a culture, what makes possible their application as fluorescent dyes in vivo.

Size of a Molecule

Low molecular weight (and therefore molecular size) is a unique feature of the compounds of the formula I in comparison with other fluorophores with similar spectral characteristics. Bathochromic shift of absorption spectra and fluorescence excitation and emission spectra is inevitably connected with the increase in molecular mass, as this shift is a consequence of the increasing the size of conjugated system of double bonds.

Thus, for green dyes, at emission maximum starting from 485 nm (compound p-HOBDI-BF2, neutral form) going to 532 nm (compound di-F-p-HOBDI-BF2, anionic form) compounds of the invention may have molecular mass up to 350 Da. Meanwhile for widely used fluorescent dyes with emission peaks in range 500-530 nm molecular masses are bigger: Alexa 488 (519 nm, 643 Da), Cy2 (506 nm, 714 Da), DiO (501 nm, >400 Da), FITC (521 nm, 389 Da), Sytox Green (523 nm, ~600 Da), FluorX (520 nm, 587 Da), fluorescein (519 nm, 389 Da). (Approximate values are given for the dyes with different substituents for binding to other molecules.)

For more red-shifted dyes, with emission peak starting from 532 nm (compound p-NH2-BDI-BF2 ((Z)-4-(4-amino-2-(difluoroboryl)benzylidene)-1,2-dimethyl-1H-imidazole-5(4H)-one)) going to 598 nm (compound p-diethylamino-BDI-dimethylaminoethenyl-BF2 ((Z)-4-(4-(diethylamino)-2-(difluoroboryl)benzylidene)-2-((E)-2-(dimethylamino)vynil)1-methyl-1H-imidazole-5(4H)-one)), compounds may have molecular mass up to 400 Da. Meanwhile analogs Cy3 (570 nm, 767 Da), Cy3.5 (594 nm, 1102 Da), Pacific Orange (551 nm, ~500 Da), DyLight 550 (576 nm, 985 Da), FluoProbes547H (574 nm, 736 Da) have significantly greater molecular masses.

Chemical Stability

Compound of the general formula I differ from the majority of fluorescent dyes because of their high resistance to the action of different chemical factors—nucleophiles and high pH. Thus, incubation at pH 11 and temperature 70° C. during 2 hours doesn't affect significantly the absorption and emission spectra of p-HOBDI-BF2. It should be noted, that long-time heating in alkaline conditions may result in exchange of fluorine atoms from difluoroboryl residue to hydroxyl groups, however no significant change in absorption and fluorescence spectra is observed.

Staining the Cell Membranes

Compounds of the current invention can be used for staining the lipid membranes, including cell membranes, including plasma membranes, intracellular membranes, nuclear membrane. Staining is possible because of high affinity of compounds with the formula I, in which $R_1$, $R_2$, $R_3$, $R_4$ independently mean hydrogen, halogen, $C_{1-6}$ alkyl substituted aminogroup, where substituents not necessarily form cyclic derivatives of pyrrol and pyrrolidine, or $C_{4-6}$ cycloalkyl substituted aminogroup, or $C_{1-6}$ alkyl alkoxyl group, for example, p-diethylamino-BDI-BF2, (Z)-4-(4-(diethylamino-2-(difluoroboryl)benzylidene)-1,2-dimethyl-1H-imidazole-5(4H)-one, to organic solvents and lipids, and accumulation of the indicated compounds in cell membranes. Suchlike staining can be carried out in cell cultures or in histological samples in particular. For staining the membranes the compounds of the present invention should be added to cell cultures, and cells should be incubated for several seconds. Stained membranes can be visualized with the use of fluorescent microscopy, as known at the moment and is shown in example 9 below.

Compound (Z)-4-(4-(diethylamino-2-(difluoroboryl)benzylidene)-1,2-dimethyl-1H-imidazole-5(4H)-one has low quantum yield of fluorescence in water solutions (0.05). Meanwhile in organic solvents quantum yield of fluorescence of p-diethylamino-BDI-BF2 increases to 0.2-0.35. Significant hypsochromic shift in fluorescence and absorption spectra is also observed at transfer from water to organic solvents. For example, in water p-diethylamino-BDI-BF2 has absorption and emission peaks at 518 nm and 562 nm, but in acetonitrile—at 493 nm and 553 nm respectively. These properties can be used for fluorescent dyeing of cell membranes. Detection of fluorescence in green and yellow channels (for example, excitation at 488 nm, detection at 500-540 nm) shows difference in the brightness of fluorescence of p-diethylamino-BDI-BF2 in water and organic phases in more than 10 times. Moreover, as p-diethylamino-BDI-BF2 has high affinity to organic solvents, then it has a tendency to accumulate in cell membranes.

It has been shown that the brightness of fluorescence of p-diethylamino-BDI-BF2 in cell membranes is almost the same as of EGFP (see Example 9). At the same time, photostability of p-diethylamino-BDI-BF2 signal is much higher than that of EGFP. The authors of the current invention assume that high photostability of p-diethylamino-BDI-BF2 could be probably explained by constant exchange between bound and non-bound dye. High brightness and very high photostability of fluorescence of the compound p-diethylamino-BDI-BF2 allow to obtain the images of intracellular membrane structures of high quality.

Moreover, the dying of cells by low concentrations of p-diethylamino-BDI-BF2 (1-10 nM) can be used for obtaining images of membrane structures in high resolution due to observation of fluorescence of single molecules of the dye p-diethylamino-BDI-BF2, becoming fluorescent in a membrane, and further highly precise calculation of the center of localization of such molecules. Examples of methods of high-resolution microscopy are given in [W. E. Moerner, D. P. Fromm, *Rev. Sci. Inst.*, 74, 8 (2003)], [C. Joo, H. Balci, Y. Ishitsuka, C. Buranachai, *Ann. Rev. Biochem.*, 77, 51 (2008)], [S. Yasushi, T. Yanagida, *Nat. Rev. Mol. Cell. Biol.*, 4, 1 (2003)].

Labeling of Biomolecules

The indicated compounds can be used for labeling of biomolecules. The compounds can be covalently (or non-covalently) attached to a biomolecule with conservation of their fluorescent properties.

Various peptides and proteins, nucleic acids and their fragments, carbohydrates, lipids, and other biomolecules can be labeled. As a result the data about their metabolism and localization in different biological system can be obtained. Labeled biomolecules can be used, in particular, for immunochemical staining, fluorescent hybridization in situ, cell labeling and finding of receptors.

Natural and artificial materials, which specifically bind biomolecules, can be labeled by compounds from the invention, which also allows to observe presence, localization and transport of biomolecules in vivo. For example, labeled substrates or inhibitors of various enzymes allow to observe the localization of the proteins, the transport of corresponding labeled enzymes and also to evaluate their expression [Griffin R J, Williams B W, Bischof J C, Olin M, Johnson G L, Lee B W. *Technol Cancer Res Treat.* 6(6), 651-4 (2007), P. A. Amstad, G. Yu, G. L. Johnson, B. W. Lee, S. Dhawan, and D. J. Phelps *BioTechniques.* 31:608-616 (2001), Jakobsen R K; Ono S; Powers J C.; DeLotto R, *Histochem Cell Biol.* 123(1): 51-60. (2005)]. Substrates and cofactors, labeled with a fluorescent compound from the present invention, can also be applied, for example, for estimation of protein function inhibition by different substances by inhibition of protein binding to a labeled substrate or cofactor [Natarajan A, Moerke N, Fan Y H, Chen H, Christ W J, Wagner G, Halperin J A. Bioorg Med Chem Lett. 17; 14(10):2657-60 (2004)]. Also compounds from the invention may be used to label antibodies and their fragments, as it is known from literature [Roederer M. Conjugation of monoclonal antibodies (2004) http://www.drmr.com/abcon/]. Labeled antibodies can be applied in different ways, including, for example, staining of cells of a particular type according to the markers on their surface, in this case detection of fluorescent staining can be carried out by fluorescent microscopy or flowing cytofluorometry, as it is well known for experts in the field of cell biology. Also hormones can be labeled to detect the presence of specific receptors on the cell surface [Shechter Y, Schlessinger J, Jacobs S, Chang K J, Cuatrecasas P. *Proc. Natl. Acad. Sci. USA* 75(5), 2135-2139, (1978)]. Compounds from the invention could also be used for labeling of proteins, specifically binding, for example, lipid rafts, and that could be used for fluorescent staining of these rafts [Chazotte B. Cold Spring Harb Protoc. 2011(5), (2011)]. DNA and RNA molecules can be labeled covalently by compounds from the invention, as it is described in [Proudnikov D, Mirzabekov A. *Nucleic Acids Res.* 24(22):4535-42 (1996), Juskowiak B., *Anal Bioanal Chem.* 399(9):3157-76 (2011), Dirsch O, Ji Y, Bohr J, Shen K, Levison D, Dahmen U., *Appl Immunohistochem Mol Morphol.* 15(3):332-7 (2007)], they could be used, for example, as fluorescent probes for in situ hybridization and staining of specific DNA and RNA in gel [Kricka L J, Fortina P., *Clin Chem.* 55(4):670-83 (2009)].

Covalent labeling by compounds of the invention could be used in lipids, that will allow to stain membranes and investigate phospholipids in them [Chazotte B. Cold Spring Harb Protoc. 2011(5), (2011)] In particular, obtaining of stained membrane components, for example, lipids, will allow to evaluate their partition in membrane layers due to the fluorescence intensity. Sugars, also in vivo, can be labeled covalently as well. The methods to label sugars by fluorescent dyes in vivo are well known, they include 1) incubation of cell with sugar derivative, containing reactive group 2) including sugar derivative in oligosaccharides on cell surface 3) labeling of oligosaccharides on cell surface with addition of a fluorescent dye, bearing a reactive group, able to react in specific conditions with the reactive group in a sugar derivative [Zheng, T.; Jiang, H.; Gros, M., Soriano del Amo, D.; Sundaram, S.; Lauvau, G.; Marlow, F.; Liu, Y., Stanley, P.; Wu, P. *Angew. Chem. Int.* Ed., 50:4113 (2011), Dehnert, K. W.; Beahm, B. J.; Huynh, T. T.; Baskin, J. M.; Laughlin, S. T.; Wang, W.; Peng Wu, P.; Amacher, S. L.; Bertozzi, C. R. *ACS Chem. Bio.* 6:547 (2011)].

The biomolecules' labeling by compounds of the invention can also be performed in methods of fluorescent resonance energy transfer (FRET). In these methods, the indicated compounds serve as donors and/or acceptors in combination with another dye or fluorescent protein, as described, for example, in Matz et al., *Nature Biotechnology* 17:969-973 (1999); green fluorescent protein from *Aequorea victoria* and its fluorescent mutant, as described in the U.S. Pat. Nos. 6,066,476; 6,020,192; 5,985,577; 5,976,796; 5,968,750; 5,968,738; 5,958,713; 5,919,445; 5,874,304; other fluorescent dyes, such as coumarin and its derivatives, 7-amino-4-methylcoumarin and aminocoumarin; dyes for live tissues; cascade blue; or fluorescein and its derivatives, such as fluorescein isothyocyanate and Oregon green; rhodamine dyes, such as Texas red, tetramethylrhodamine, eosines and erythrosines; cyano dyes, such as Cy3 and Cy5; macrocyclic chelates of lanthanide ions. Obtained pairs of donor and acceptor for FRET, one of which is a compound from the invention, can be applied for detection of interactions, including protein-ligand interactions [Xie N, Elangwe E N, Asher S, Zheng Y G. *Bioconjug Chem.* 20(2):360-6 (2009)] and protein-protein interactions [Keppler A, Pick H, Arrivoli C, Vogel H, Johnsson K. *Proc Natl Acad Sci USA.* 101(27):9955-9 (2004)]. Also utilization of the invented compounds for FRET implies obtaining analogs of enzyme substrates, for which enzyme activity causes the loss of FRET [Wichmann O, Gelb M H, Schultz C. Chembiochem. 8(13):1555-69 (2007)]. Another example of FRET use is PCR as a real-time process. DNA fragment is labeled, but during the progress of PCR the labeled fragment and the fragment, containing a compound, which inhibits fluorescence, separate in space, and this causes the increase in fluorescence signal [H. D. VanGuilder, K. E. Vrana, W. M. Freeman, *Biotechniques,* 44 (5), 619 (2008)].

One of the distinctive features of compounds with the formula I is that they can be easily chemically modified. Various modifications of such compounds shall take place either before difluoroboryl substituent introduction (see Examples 2,4) or in further steps (see Examples 3,5).

As a result of such modification, various substituents can be introduced into a molecule, allowing the chemical binding for labeling of different molecules-substrates. Carbonyl group (see Example 3), amino group, isocyanate, isothiocyanate, alcohol of thiol, azide or acetylene fragments can be used in this role.

Use of a fluorescent derivative and a corresponding procedure of chemical binding is directly connected to the structure of a chosen substrate molecule-. The majority of biological objects have free amino or carbonyl groups in their structure, which allows to use a peptide synthesis technology for obtaining the corresponding amides [S. B. H. Kent, *Ann. Rev. Biochem.*, 57, 957 (1988)], [F. Guzmán, S. Barberis, A. Illanes, *Electronic Journal of Biotechnology*, 10(2), 15 (2007)]. Meanwhile, amino groups and alcohol or thiol groups may be modified with isocyanate or isothiocyanate derivatives. The utilization of artificial non-biological substrates significantly widens the possibilities of such modifications, as artificial objects can deliberately contain different functional groups, able to bind with a dye. Thus, the methods of so-called "click chemistry" became very popular [H. C. Kolb, M. G. Finn, K. B. Sharpless, *Ang. Chem. Int. Ed.*, 40(11), 2004 (2001)]—dipolar [2+3] cycloaddition of terminal acetylenes to organic azides with copper as a catalyst.

EXAMPLES

Example 1

Synthesis of (Z)-4-(2-(difluoroboryl)-4-hydroxybenzylidene)-1,2-dimethyl-1H-imidazole-5(4H)-one (Table 1, compound 2)

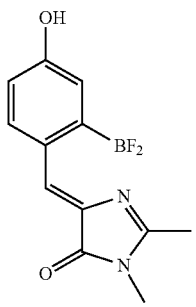

Stage 1

Synthesis of (Z)-4-(4-((tertbutyldiphenyl)oxy)benzylidene-1,2-dimethyl-1H-imidazole-5(4H)-one The solution of ((Z)-4-(4-hydroxybenzylidene)-1,2-dimethyl-1H-imidazole-5(4H)-one [S. Kojima, H. Ohkawa, N. Hirano, S. Maki, H. Niwa, M. Ohashi, S. Inouye, F. I. Tsuji, *Tetr. Lett.*, 39, 5239 (1998)] (4.3 g, 20.0 mmol), diphenyl (tert.butyl)chlorosilane (7.2 g, 26.2 mmol), diisopropylethylamine (3.9 g, 30.2 mmol) and imidazole (140 mg, 2.1 mmol) in dry tetrohydrofurane (200 mL) was stirred for 30 hours. Then the reaction mixture was evaporated, dissolved in 300 mL of chloroform, washed with hydrochloric acid (5%, 100 mL) and water (2×100 mL). The solution was dried over anhydrous sodium sulfate, evaporated and the product purified by column chromatography (chloroform): 7.65 g (Yield 84%)

$^1$H NMR (DMSO-$d_6$) δ 8.00 (d, 2H, J=8.76 Hz), 7.67 (d, 4H, J=6.72 Hz), 7.49 (t, 2H, J=7.48 Hz), 7.44 (d, 4H, J=7.48 Hz), 6.85 (s, 1H), 6.78 (d, 2H, J=8.76 Hz), 3.06 (s, 3H), 2.30 (s, 3H), 1.05 (s, 9H).

$^{13}$C NMR (DMSO-$d_6$) δ 15.72 (CH$_3$), 19.41, 26.66 (CH$_3$), 26.75 (3*CH$_3$), 120.17 (2*CH), 124.85, 128.16, 128.59 (4*CH), 130.82 (2*CH), 132.22 (CH), 134.06 (2*CH), 135.49 (4*CH), 137.91, 157.08, 163.79, 170.24.

HRMS (ESI) calculated for $C_{28}H_{31}N_2O_2Si$ 455.2155. found 455.2142.

Stage 2

Synthesis of ((Z)-4-(2-(difluoroboryl)4-hydroxybenzylidene)-1,2-dimethyl-1H-imidazole-5(4H)-one (Z)-4-(4-((tertbutyldiphenyl)oxy)benzylidene-1,2-dimethyl-1H-imidazole-5(4H)-one (1.36 g, 3.0 mmol) was dissolved in dichloromethane (50 mL), commercially available molecular sieves were added (6 g 3 Å and 6 g 4 Å), then the solution of boron tribromide in dichloromethane (1M, 12 mL, 12 mmol) was added. The reaction mixture was stirred for 120 hours at r.t., then diluted by dichloromethane (150 mL), washed with aqueous NaHCO$_3$ (50 мL), water (2×100 mL) and dried over Na$_2$SO$_4$. The solvent was evaporated, the remaining residue dissolved in 200 mL of the solution of tetrabutylammonium fluoride trihydrate (3.2 g, 10 mmol) in ethylacetate. The reaction mixture was stirred for 10 min at r.t. then neutralized by acetic acid (1 mL), washed with water (2×50 мл) and concentrated NaCl solution (2×50 мл). The organic phase was dried over anhydrous sodium sulfate, evaporated and purified by column chromatography (ethyl acetate-hexane 4:1, neutral aluminum oxide): 330 mg. (Yield 42%)

$^1$H NMR (DMSO-$d_6$) δ 10.2 (s, 1H, OH), 7.56 (s, 1H), 7.48 (d, 1H, J=8.31 Hz), 7.00 (d, 1H, J=2.20 Hz), 6.74 (dd, 1H, J$_1$=8.31 Hz, J$_2$=2.45 Hz), 3.22 (s, 3H), 2.71 (s, 3H).

$^{13}$C NMR (DMSO-$d_6$) δ 13.38 (CH$_3$), 26.96 (CH$_3$), 115.63 (CH), 118.98 (CH), 124.50, 125.36, 129.72 (CH), 134.79 (CH), 161.92, 163.27, 165.25.

HRMS (ESI) calculated for $C_{12}H_{12}BF_2N_2O_2$ 265.0960. found 265.0951.

Example 2

Synthesis of (Z)-4-(2-(difluoroboryl)-5-fluoro-4-hydroxybenzylidene)-1,2-dimethyl-1H-imidazole-5 (4H)-one (Table 1, compound 2)

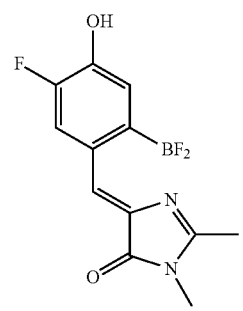

Stage 1

Synthesis of (Z)-4-(3-fluoro-4-hydroxybenzylidene)-2-methyloxazole-5(4H)-one Commercially available 3-fluoro-4-hydroxybenzaldehyde (14 g, 0.1 mol), N-acetylglycine (14 g, 0.12 mol), sodium carbonate (10.6 g, 0.1 mol) and sodium acetate (16.6 g, 0.2 mol) were mixed at r.t. in 60 mL of acetic anhydride and stirred at moderate heating until full dissolution of carbonate. Then the mixture was refluxed for 2 hours, cooled down to r.t. and diluted with water (200 mL). The precipitate was filtered and used without further purification: 22.34 g. (Yield ~85%)

$^1$H NMR (CDCl$_3$) δ 7.51 (m, 2H), 7.43 (d, J=11.0 Hz, 1H), 6.90 (t, J=7.3 Hz, 1H), 6.55 (m, 1H), 2.24 (s, 3H).

Stage 2

Synthesis of ((Z)-4-(3-fluoro-4-hydroxybenzylidene)-1,2-dimethyl-1H-imidazole-5(4H)-one (Z)-4-(3-fluoro-4-hydroxybenzylidene)-2-methyloxazole-5(4H)-one (13.2 g, 0.05 mol) was suspended in ethanol (100 mL), and water solution of methylamine (40%, 11.6 g, 0.15 mol) was added. The reaction mixture was stirred at r.t. for 2 hours, then potassium carbonate (13.8 g, 0.1 mol) was added, and the mixture refluxed for 4 hours. Then it was cooled down to r.t., diluted with water (400 mL) and acidified with HCl (10% in water) until the precipitate stopped to form. The precipitate was filtered, washed with cold (−20° C.) ethanol, then diethyl ether and dried under vacuum: 8.78 g. (Yield 75%)

$^1$H NMR (DMSO-d$_6$) δ 8.22 (m, 1H), 7.76 (m, 1H), 6.99 (t, J=8.76 Hz, 1H), 6.89 (s, 1H), 3.09 (s, 3H), 2.34 (s, 3H).

$^{13}$C NMR (DMSO-d$_6$) δ 15.31, 26.17, 115.05 (m), 122.68, 124.71, 135.57 (m), 138.37, 151.09 (m), 152.46 (m), 164.31, 169.52.

HRMS (ESI) calculated for C$_{12}$H$_{12}$FN$_2$O$_2$: 235.0883. found [M+H]=235.090

Stage 3

Synthesis of (Z)-4-(2-(difluoroboryl)-5-fluoro-4-hydroxybenzylidene)-1,2-dimethyl-1H-imidazole-5(4H)-one ((Z)-4-(3-fluoro-4-hydroxybenzylidene)-1,2-dimethyl-1H-imidazole-5(4H)-one (11.7 g, 0.05 mol) was mixed with commercially available molecular sieves (35 g 3 Å and 35 g 4 Å) in 300 mL, of dichloroethane. Solution of BBr$_3$ (1M in dichloroethane, 200 mL, 0.2 mol) was added, the reaction mixture was refluxed for 6 hours, then cooled down, filtered, washed with cold ethanol (100 mL). To the solution HF was added (20% in water, 50 mL), the mixture was stirred for 30 min, then diluted with ethyl acetate (500 mL) and washed with water (2×200 mL), saturated sodium carbonate solution (2×200 mL) and saturated sodium chloride solution (2×100 mL). The organic phase was dried over anhydrous sodium sulfate, evaporated and purified by column chromatography (chloroform:ethanol—10:1): 5.1 g. (Yield 36%)

$^1$H NMR (DMSO-d$_6$) δ 10.64 (s, 1H), 7.55 (s, 1H), 7.47 (d, J=12.06 Hz, 1H), 7.15 (d, J=9.43 Hz, 1H), 3.22 (s, 3H), 2.72 (s, 3H).

$^{13}$C NMR (DMSO-d$_6$) δ 12.90, 26.46, 118.56 (m), 120.37, 124.98, 125.22, 127.81, 148.8 (m), 150.9 (m), 162.67, 165.92.

HRMS (ESI) calculated for C$_{12}$H$_{11}$BF$_3$N$_2$O$_2$: 283.0866. found [M+H]=283.088

Example 3

Synthesis of (Z)-4-(4-(diethylamino)-2-(difluoroboryl)benzylidene)-1-methyl-2-((E)-steryl)-1H-imidazole-5(4H)-one (Table 1, compound 11)

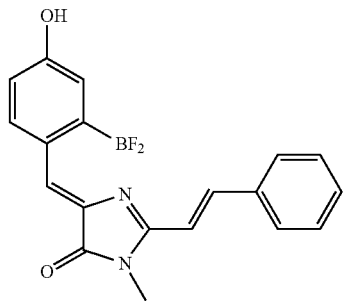

Stage 1

Synthesis of (Z)-4-(4-(diethylamino)-2-(difluoroboryl)benzylidene)-1-methyl-2-((E)-steryl)-1H-imidazole-5(4H)-one (Z)-4-(4-(diethylamino)-2-(difluoroboryl)benzylidene)-1,2-dimethyl-1H-imidazole-5(4H)-one (3.2 g, 10 mmol), synthesized in the same manner as the compound in example 1, was dissolved in dry tetrahydrofurane (20 mL), commercially available benzaldehyde (2.1 g, 20 mmol) and anhydrous zinc chloride (0.68 g, 5 mmol) were added. The reaction mixture was heated in a closed container up to 80° C. and stirred for 3 hours. Then the mixture was cooled down, diluted with ethyl acetate (200 mL) and washed with sodium carbonate solution (5% in water, 50 mL), water (2×50 mL) and saturated sodium chloride solution (2×50 mL). The organic phase was dried over anhydrous sodium sulfate, evaporated and purified by column chromatography (chloroform:ethanol—10:1): 2.9 g. (Yield 71%)

$^1$H NMR (DMSO-d$_6$) δ 8.13 (d, J=8.8 Hz, 2H), 7.76 (d, J=8.07 Hz, 2H), 7.68 (d, J=14.75 Hz, 1H), 7.47 (t, J=8.55 Hz, 2H), 7.42 (m, 3H), 7.13 (m, 2H), 6.73 (d, J=8.80 Hz, 2H), 3.33 (s, 3H), 3.30 (q, J=7.05 Hz, 4H), 1.17 (t, J=7.05 Hz, 6H).

$^{13}$C NMR (CDCl$_3$-DMSO-d$_6$) δ 12.29, 28.05, 45.28, 114.06, 115.35, 116.52, 118.23, 124.68, 128.40, 128.96, 129.73, 131.46, 132.50, 135.58, 141.09, 149.06, 158.02, 159.83, 166.47.

HRMS (ESI) calculated for C$_{23}$H$_{25}$BF$_2$N$_3$O: 408.2059. found [M+H]=408.204

Example 4

Synthesis of (Z)-4-(4-(2-(difluoroboryl)-4-hydroxybenzylidene)-2-methyl-5-oxo-4,5-dihydro-1H-imidazole-1-yl)butanoic acid (Table 1, compound 10)

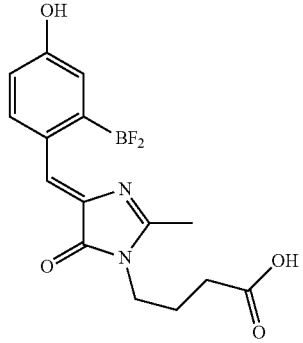

Stage 1

Synthesis of (Z)-4-(4-(4-hydroxybenzylidene)-2-methyl-5-oxo-4,5-dihydro-1H-imidazole-1-yl)butanoic acid (Z)-4-(3-fluoro)-4-hydroxybenzylidene)-2-methyloxazole-5(4H)-one (7.35 g, 30.0 mmol), obtained in the same manner as in example 1, was suspended in ethanol (150 mL), and a mixture of γ-aminobutyric acid (9.27 g, 90.0 mmol), triethylamine (7.58 g, 75.0 mmol) and water (10 mL) was added. The reaction mixture was stirred at r.t. for 3 hours, then evaporated. The residue was dissolved in DMF (80 mL), cesium carbonate was added (3.26 g, 10 mmol) and the mixture was refluxed for 15 minutes. Then the solvent was evaporated, and the resulting residue was dissolved in water (100 mL), acidified (pH~5) and extracted with ethyl acetate (3×300 мл). Organic phase was washed with water (1×50 mL) and concentrated sodium chloride solution (5×50 мл), then dried over anhydrous sodium sulfate and evaporated. The resulting precipitate was washed with cold (−20° C.) ethanol, diethyl ether and dried under vacuum: 7.6 g. (Yield 88%)

$^1$H NMR (DMSO-$d_6$) δ 12.10 (s, 1H), 10.10 (s, 1H), 8.07 (d, J=8.77 Hz, 2H), 6.88 (s, 1H), 6.83 (d, J=8.77 Hz, 2H), 3.58 (t, J=7.23 Hz, 2H), 2.35 (s, 3H), 2.26 (t, J=7.02 Hz, 2H), 1.78 (m, J=7.02 Hz, 2H).

$^{13}$C NMR (DMSO-$d_6$) δ 15.14 ($CH_2$), 23.93 ($CH_2$), 30.67 ($CH_2$), 39.23 ($CH_3$), 115.71 (2CH), 125.28, 125.60 (CH), 134.06 (2CH), 159.57, 161.74, 169.82, 173.71.

HRMS (ESI) calculated for $C_{15}H_{17}N_2O_4$: 289.1188. found [M+H]=289.122

Stage 2

Synthesis of (Z)-tert.butyldiphenyl-4-(4-(4-((tert.butyldiphenysilyl)oxy)benzylidene)-2-methyl-5-oxo-4,5-dihydro-1H-imidazole-1-yl)butyrate The solution of (Z)-4-(4-(4-hydroxybenzylidene)-2-methyl-5-oxo-4,5-dihydro-1H-imidazole-1-yl)butanoic acid (7.20 g, 25.0 mmol), diphenyl(tert.butyl)chlorosilane (16.50 g, 60.0 mmol), diisopropylethylamine (9.68 g, 75.0 mmol) and imidazole (167 mg, 2.5 mmol) in dry tetrahydrofurane (250 mL) was stirred for 30 hours at r.t. Then the solvent was evaporated, resulting residue was dissolved in 500 mL of ethyl acetate. The organic phase was washed with HCl solution (5% in water, 150 mL), water (2×100 mL) and saturated NaCl solution (5×50 мл), then dried over anhydrous sodium sulfate and evaporated. The remained residue was purified by column chromatography (ethyl acetate:heptane—1:3): 15.28 g. (Yield 80%)

$^1$H NMR (CDCl$_3$) δ 7.95 (d, J=8.80 Hz, 2H), 7.74 (d, J=8.07 Hz, 4H), 7.70 (d, J=8.07 Hz, 4H), 7.45 (t, J=7.34 Hz, 4H), 7.40 (m, 8H), 7.03 (s, 1H), 6.83 (d, J=8.80 Hz, 2H), 3.63 (t, J=7.34 Hz, 2H), 2.26 (t, J=6.84 Hz, 2H), 2.27 (s, 3H), 1.96 (m, J=6.84 Hz, 2H), 1.14 (s, 9H), 1.13 (s, 9H).

$^{13}$C NMR (CDCl$_3$) δ 15.46 ($CH_2$), 19.06, 19.42, 24.45 ($CH_2$), 26.42 (3$CH_3$), 26.85 (3$CH_3$), 32.65 ($CH_2$), 39.52 ($CH_3$), 120.18 (2CH), 127.43, 127.46. 127.62, 127.71 (4CH), 127.82 (4CH), 130.00 (2CH), 130.10 (2CH), 131.67 (CH), 133.81 (2CH), 135.27 (4CH), 135.39 (4CH), 157.64, 161.01, 170.68, 171.88.

HRMS (ESI) calculated for $C_{47}H_{53}N_2O_4Si_2$: 765.3544. found [M+H]=765.360

Stage 3

Synthesis of (Z)-ethyl-4-(4-(2-(difluoroboryl)-4-hydroxybenzylidene)-2-methyl-5-oxo-4,5-dihydro-1H-imidazole-1-yl)butyrate (Z)-tert.butyldiphenyl-4-(4-(4-((tert.butyldiphenysilyl)oxy)benzylidene)-2-methyl-5-oxo-4,5-dihydro-1H-imidazole-1-yl)butyrate (15.28 g, 20.0 mmol) was mixed with commercially available molecular sieves (20 g 3 Å and 20 g 4 Å) in 150 mL of dichloroethane. The solution of BBr$_3$ (1M in dichloromethane, 100 mL, 0.1 mol) was added, and the reaction mixture was stirred for 120 hours at r.t. The resulting mixture was filtrated, the sieves were washed with dichloromethane (3×100 mL), the solvent was evaporated. The oil was dissolved in dry tetrahydrofurane (200 mL) and ethanol (100 mL). The mixture was stirred for 20 minutes, then saturated HF solution was added (20 mL). In 20 minutes the solvent was partially evaporated (3-4 times), the residue was dissolved in ethyl acetate (400 mL), washed with water (5×100 mL), aqueous sodium carbonate (5%, 2×100 mL) and brine (2×50 mL). The organic phase was dried over anhydrous sodium sulfate, evaporated and purified by column chromatography (chloroform:ethanol—10:1): 2.62 g. (Yield 36%)

$^1$H NMR (DMSO-$d_6$) δ 11.03 (s, 1H), 10.22 (s, 1H), 7.55 (s, 1H), 7.49 (d, J=8.33 Hz, 1H), 7.01 (d, J=2.19 Hz, 1H), 6.74 (dd, $J_1$=8.33 Hz, $J_2$=2.19 Hz, 1H), 4.02 (q, J=7.02 Hz, 2H), 3.75 (t, J=7.23 Hz, 2H), 2.74 (s, 3H), 2.40 (t, J=7.02 Hz, 2H), 1.89 (m, J=7.02 Hz, 2H), 1.16 (t, J=7.02 Hz, 3H).

$^{13}$C NMR (DMSO-$d_6$) δ 12.61 ($CH_2$), 13.97 ($CH_3$), 23.02 ($CH_2$), 30.56 ($CH_2$), 40.42 ($CH_3$), 59.91 ($CH_2$), 115.14 (CH), 118.50 (CH), 123.87, 124.84 (m), 129.41 (CH), 134.33 (CH), 161.47, 162.86, 164.11, 172.19.

HRMS (ESI) calculated for $C_{17}H_{20}BF_2N_2O_4$: 365.1484. найдено [M+H]=365.152

Stage 4

Synthesis of (Z)-4-(4-(2-(difluoroboryl)-4-hydroxybenzylidene)-2-methyl-5-oxo-4,5-dihydro-1H-imidazole-1-yl)butanoic acid (Z)-ethyl-4-(4-(2-(difluoroboryl)-4-hydroxybenzylidene)-2-methyl-5-oxo-4,5-dihydro-1H-imidazole-1-yl)butyrate (1.82 g, 5.0 mmol) was dissolved in water (200 mL), then ethanol (50 mL) and sodium hydroxide (400 mg, 10.0 mmol) were added. The mixture was stirred for 2 hours at r.t., then acidified with aqueous HF solution and extracted with ethyl acetate (3×100 mL), washed with water (1×50 mL) and dried over anhydrous sodium sulfate. The mixture was evaporated and purified by column chromatography (chloroform:ethanol—5:1): 1.29 g. (Yield 77%)

$^1$H NMR (DMSO-$d_6$) δ 11.88 (s, 1H), 10.30 (s, 1H), 7.55 (s, 1H), 7.49 (d, J=8.2 Hz, 1H), 7.00 (d, J=2.2 Hz, 1H), 6.74 (dd, $J_1$=8.2 Hz, $J_2$=2.2 Hz, 1H), 3.75 (t, J=7.23 Hz, 2H), 2.754 (s, 3H), 2.32 (t, J=7.02 Hz, 2H), 1.85 (m, J=7.02 Hz, 2H).

$^{13}$C NMR (DMSO-$d_6$) δ 12.61 ($CH_2$), 23.13 ($CH_2$), 30.67 ($CH_2$), 40.42 ($CH_3$), 115.12 (CH), 118.48 (CH), 123.86, 124.65 (m), 129.38 (CH), 134.29 (CH), 161.47, 162.85, 164.14, 173.71.

HRMS (ESI) calculated for $C_{15}H_{15}BF_2N_2O_4$: 336.1093. calculated (M+Na) 359.0988. found [M+Na]=359.098

Example 5

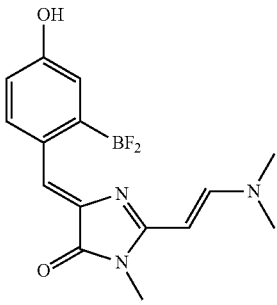

Synthesis of (Z)-4-(2-(difluoroboryl)-4-hydroxybenzylidene)-2-((E)-2-(dimethylamino)vynil)-1-methyl-1H-imidazole-5(4H)-one (table 1, compound 8)

(Z)-4-(2-(difluoroboryl)-4-hydroxybenzylidene)-1,2-dimethyl-1H-imidazole-5(4H)-one (264 mg, 1 mmol), obtained in the same manner as in example 1, was dissolved in dry DMF (5 mL), and commercially available dimethylformamide diethylacetal (1 g, 6.8 mmol) was added. The reaction mixture was heated in a closed container up to 120° C. and stirred for 2 minutes, then cooled down, evaporated and purified with column chromatography (chloroform:ethanol—10:1): 266 mg. (Yield 83%)

$^1$H NMR (DMSO-$d_6$) δ 9.67 (s, 1H), 8.70 (d, J=10.8 Hz, 1H), 7.28 (d, J=8.1 Hz, 1H), 6.97 (m, 1H), 6.93 (s, 1H), 6.68 (m, 1H), 5.19 (d, J=10.8 Hz, 1H), 3.34 (s, 3H), 3.13 (s, 3H).

$^{13}$C NMR (CDCl$_3$-DMSO-$d_6$) δ 29.05, 41.67, 82.65, 115.37, 116.52, 119.23, 128.23, 130.54, 132.50, 142.10 (m), 158.25, 158.44, 162.63, 166.47.

HRMS (ESI) calculated for $C_{15}H_{16}BF_2N_3O_2$: 320.1382. found [M+H]=320.135

In the same manner according to the common scheme 1 the related compounds 3, 5, 6, 7, 9 from Table 1 were synthesized.

TABLE 1

The examples of compounds with Formula I and their close analog p-HOBDI

| N/N | Name | Structure | Chemical name |
|---|---|---|---|
| 1. | p-HOBDI (closest structural analog of the compounds obtained) | 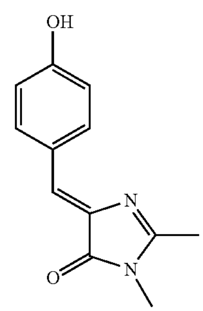 [SMILES: CC1=N/C(=C\c2ccc(O)cc2)C(=O)N1C] | (Z)-4-(4-hydroxybenzylidene)-1,2-dimethyl-1H-imidazole-5(4H)-one |
| 2. | p-HOBDI-BF2 (Example 1) | 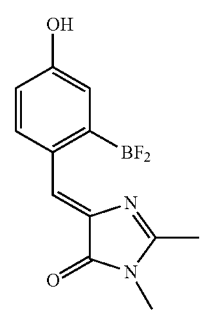 | (Z)-4-(2-(difluoroboryl)-4-hydroxybenzylidene)-1,2-dimethyl-1H-imidazole-5(4H)-one |
| 3. | di-F-p-HOBDI-BF2 | 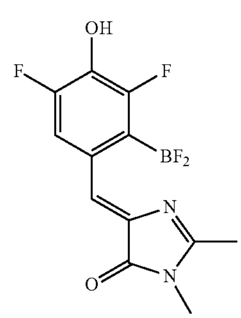 | (Z)-4-(2-(difluoroboryl)-3,5-difluoro-4-hydroxybenzylidene)-1,2-dimethyl-1H-imidazole-5(4H)-one |

TABLE 1-continued

The examples of compounds with Formula I and their close analog p-HOBDI

| N/N | Name | Structure | Chemical name |
|---|---|---|---|
| 4. | F-p-HOBDI-BF2 (Example 2) | 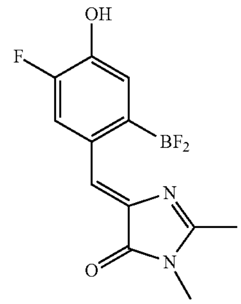 | (Z)-4-(2-(difluoroboryl)-5-fluoro-4-hydroxybenzylidene)-1,2-dimethyl-1H-imidazole-5(4H)-one |
| 5. | p-NH2-BDI-BF2 | 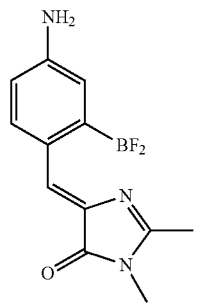 | (Z)-4-(4-amino-2-(difluoroboryl)benzylidene)-1,2-dimethyl-1H-imidazole-5(4H)-one |
| 6. | p-diethylamino-BDI-BF2 | 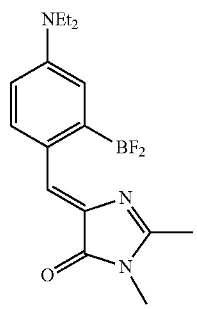 | (Z)-4-(4-(diethylamino)-2-(difluoroboryl)benzylidene)-1,2-dimethyl-1H-imidazole-5(4H)-one |
| 7. | p-dimethylamino-BDI-BF2 | 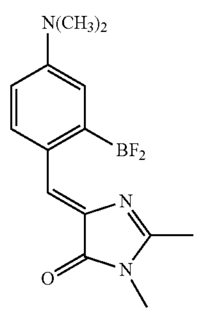 | (Z)-4-(4-(dimethylamino)-2-(difluoroboryl)benzylidene)-1,2-dimethyl-1H-imidazole-5(4H)-one |
| 8. | p-HOBDI-dimethylaminoethenyl-BF2 | 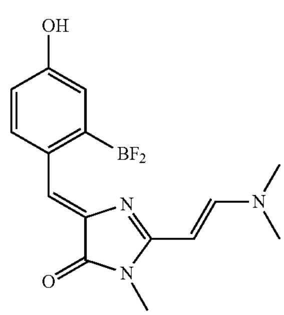 | (Z)-4-(2-(difluoroboryl)-4-hydroxybenzylidene)-2-((E)-2-(dimethylamino)vynil)-1-methyl-1H-imidazole-5(4H)-one |

TABLE 1-continued

The examples of compounds with Formula I and their close analog p-HOBDI

| N/N | Name | Structure | Chemical name |
|---|---|---|---|
| 9. | p-diethylamino-BDI-dimethylaminoethenyl-BF2 (Example 5) | 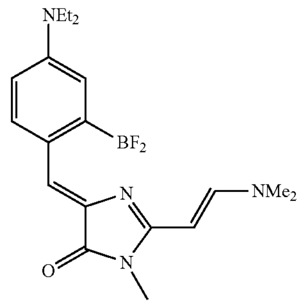 | (Z)-4-(4-(diethylamino)-2-(difluoroboryl)benzylidene)-2-((E)-2-(dimethylamino)vynil)-1-methyl-1H-imidazole-5(4H)-one |
| 10. | (Example 4) | 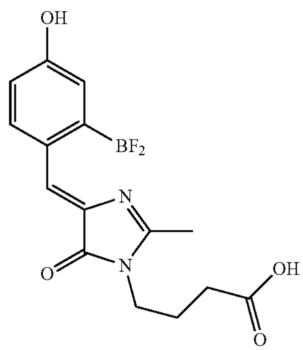 | (Z)-4-(4-(2-(difluoroboryl)-4-hydroxybenzylidene)-2-methyl-5-oxo-4,5-dihydro-1H-imidazol-1-yl)butanoic acid |
| 11. | (Example 3) | 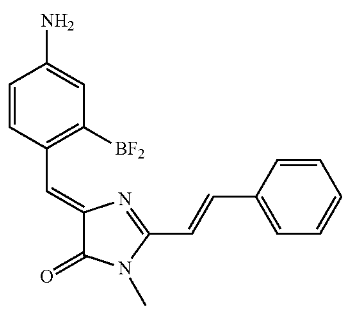 | (Z)-4-(4-(diethylamino)-2-(difluoroboryl)benzylidene)-1-methyl-2-((E)-steryl)-1H-imidazole-5(4H)-one |

Study of the Properties of the Compounds

Example 6

Measuring Spectral Characteristics of Fluorescent Dyes of the Formula I

To measure spectral characteristics of some compounds with the formula I weighted portions of compounds p-NH2-BDI-BF2, p-dimethylamino-BDI-BF2, p-diethylamino-BDI-BF2, p-HOBDI-BF2, di-F-p-HOBDI-BF2, p-diethylamino-BDI-dimethylaminoethenyl-BF2 and p-HOBDI-dimethylaminoethenyl-BF2 were dissolved in water, ethanol and acetonitrile. Absorption spectra were measured on Varian Cary 100 Bio spectrophotometer, fluorescence spectra were measured on Varian Cary Eclipse scanning spectrofluorometer.

The values of absorption and emission maxima and molar extinction coefficients for examples of compounds with the formula I in the indicated solvents are listed in a Table 2.

Emission peaks of the investigated compounds settle into a rather wide range from 485 nm for p-HOBDI-BF2 to 598 nm for p-diethylamino-BDI-dimethylamino-ethenyl-BF2.

For compounds p-NH2-BDI-BF2, p-dimethylamino-BDI-BF2, p-diethylamino-BDI-BF2, p-HOBDI-BDI-BF2 in neutral form, di-F-p-HOBDI-BF2 in neutral form, F-p-HOBDI-BF2 in neutral form, p-diethylamino-BDI-dimethylaminoethenyl-BF2 and p-HOBDI-dimethylaminoethenyl-BF2 in neutral form a hypsochromic shift of emission and absorption spectra appears with the change of more polar solvent (water) to less polar (ethanol, acetonitrile).

For compounds p-HOBDI-BF2 in anionic form, di-F-p-HOBDI-BF2 in anionic form, F-p-HOBDI-BF2 in anionic form and p-HOBDI-dimethylaminoethenyl-BF2 in anionic form a bathochromic shift of emission and absorption spectra appears with the change of more polar solvent (water) to less polar (ethanol, acetonitrile).

TABLE 2

Emission and absorption maxima (nm) of the examples of compounds with the formula I in different solvents.

| Compound | Water Abs. peak, nm (ext. coef.) | Water Emis. peak, nm | ethanol Abs. peak, nm (ext. coef.) | ethanol Emis. peak, nm | acetonitrile Abs. peak, nm (ext. coef.) | acetonitrile Emis. peak, nm |
|---|---|---|---|---|---|---|
| p-NH2-BDI-BF2 | 475 | 532 | 476 | 532 | 451 | 518 |
| p-dimethylamino-BDI-BF2 | 507 | 565 | 498 | 557 | 483 | 551 |
| p-diethylamino-BDI-BF2 | 514 (54000) | 562 | 506 (59000) | 558 | 493 (54000) | 553 |
| p-HOBDI-BF2 (neutral form) | 404 (26000) | 485 | 416 (25000) | 483 | 402 (31000) | 469 |
| p-HOBDI-BF2 (anionic form) | 485 (47000) | 520 | 512 (55000) | 532 | 521 | 540 |
| di-F-p-HOBDI-BF2 (anionic form) | 484 (44400) | 532 | 503 (45000) | 538 | 519 | 542 |
| di-F-p-HOBDI-BF2 (neutral form) | 400 (32000) | 532* | 400 (21000) | 538* | 392 (26000) | 460 |
| F-p-HOBDI-BF2 (anionic form) | 478 (38300) | 528 | 505 (48000) | 537 | 522 | 543 |
| F-p-HOBDI-BF2 (v) | 392 (31500) | 528* | 408 (24000) | 482 | 397 (28000) | 468 |
| p-diethylamino-BDI-dimethylaminoethenyl-BF$_2$ | 525 | 598 | 525 | 588 | 510 | 583 |
| p-HOBDI-dimethylaminoethenyl-BF$_2$ (anionic form) | 502 | 570 | 529 | 587 | 555 | 598 |
| p-HOBDI-dimethylaminoethenyl-BF$_2$ (neutral form) | 467 | 521 | 450 | 505 | 444 | 502 |

*only emission of deprotonated form can be measured due to high photoacidity.

Quantum yields of the examples of compounds with the formula I are listed in Table 3. The compounds p-NH2-BDI-BF2, p-HOBDI-BF2 (anionic form), di-Fp-HOBDI-BF2 (anionic form), p-diethylamino-BDI-dimethylaminoethenyl-BF2, p-HOBDI-dimethylaminoethenyl-BF2 (anionic form) have rather high quantum yields of fluorescence in water solutions.

Compound p-diethylamino-BDI-BF2 has low quantum yield of fluorescence in water solutions (0.05). In organic solvents quantum yield of fluorescence for p-diethylamino-BDI-BF2 increases up to 0.2-0.35. There is also a significant hypsochromic shift of absorption and fluorescence spectra when going from water to organic solvents (Table 2). These properties can be used for fluorescent staining of cell membranes.

TABLE 3

Quantum yields of the examples of compounds with the formula I and their nearest structure analog p-HOBDI.

| Compound | water | ethanol | acetonitrile |
|---|---|---|---|
| p-NH2-BDI-BF2 | 0.70 | 0.64 | 0.62 |
| p-dimethylamino-BDI-BF2 | 0.05 | 0.31 | 0.49 |
| p-diethylamino-BDI-BF2 | 0.05 | 0.22 | 0.34 |
| p-HOBDI-BF2 (anionic form) | 0.54 | No data | 0.73 |
| di-F-p-HOBDI-BF2 (anionic form) | 0.73 | No data | No data |
| p-diethylamino-BDI-dimethylaminoethenyl-BF$_2$ | 0.35 | No data | No data |
| p-HOBDI-dimethylaminoethenyl-BF$_2$ (anionic form) | 0.27 | No data | No data |
| p-HOBDI | Quantum yield is less than $10^{-4}$ [D. Mandal, T. Tahara, S.R. Meech, J. Phys. Chem. B, 108, 1102 (2004)] | | |

Example 7

The Determination of Solubility in Water and Partition Coefficient Octanol-1/Water for HOBDI-BF2, F-p-HOBDI-BF2 and di-F-p-HOBDI-BF2

To determine the solubility in water of compounds an excess amount of analyzed substance was put in a known volume of a solvent and stirred for 5 hours at r.t. The obtained mixture was centrifuged, and the concentration of a compound in mother liquor was measured with spectrophotometric method on the base of molar extinction coefficients data.

The determination of partition coefficient octanol-1/water was performed at room temperature and constant pH of the solution. Octanol-1 ACS reagent and distilled water were used. The system of mutually saturated octanole-1 and water was prepared prior to the experiment. For this equal volumes of solvents (5 mL) were mechanically mixed in a shaker during 5 hours, then left till phase separation. Saturated solution of an investigated compound in octanol-1 (preliminarily saturated with water) was also prepared in advance.

During the experiment saturated solution of a compound in octanol-1 in the quantity of 5 mL was added to the system, then the mixture was stirred for 5 hours in mechanical shaker and centrifuged till phase separation. The phase samples were prepared with a syringe, then the concentration of a compound in each was determined with spectrophotometric method on the base of molar extinction coefficients data.

The partition coefficient is defined as a value, equal to the decimal logarithm of the ratio of equilibrium concentrations of a compound dissolved in two-phase system, consisting of two immiscible solvents.

The measured solubility in water for the compounds p-HOBDI-BF2, F-p-HOBDI-BF2, di-F-p-HOBDI-BF2 is around 1 mM at acidic and neutral pH values. At weakly alkaline pH values the solubility increases many times (more than in 10 times), what is induced by transfer of the dyes to anionic form (phenol group dissociation).

For the three indicated compounds the value of partition coefficient water-octanol is more than 4 (anionic form, pH 10), which designates on their high hydrophilic nature.

Example 8

The Determination of Toxicity of Exemplary Compounds of the Formula I for Mammalian Cell Line HEK293

The solutions of the compounds p-HOBDI-BF2, F-p-HOBDI-BF2, di-F-p-HOBDI-BF2 and p-diethylamino-BDI-BF2 in DMSO were added to $2 \times 10^4$ of HEK293T line cells, cultivated in wells of 24-well plate in full medium DMEM, in a 5 μL volume on 500 μL of the medium with final concentration 10 nM, 100 nM, 1 μM and 10 μM. DMSO was also added to the cells as a control. Toxic action on the cells was measured after 24 hours: the cells were treated by trypsin and collected, the percentage of dead cells was counted on hemocytometer after trypan blue staining.

The compounds had no toxic effect on the cells of HEK293T cell line in medium at all investigated concentrations.

Example 9

The Staining of Cell Membranes of HeLa Kyoto and HEK923 Cell Lines by p-diethylamino-BDI-BF2 and Comparison of its Photostability with that of Green Fluorescent Protein EGFP To check the possibility of the compound p-diethylamino-BDI-BF2 utilization as a fluorescent marker for cell membranes staining the following experiments were carried out.

Human cell cultures HeLa and HEK293 were grown in standart conditions and analyzed by wide field fluorescent and confocal laser scanning microscopy (excitation at 488 nm, detection at 500-540 nm). After addition of the compound p-diethylamino-BDI-BF2 to the cell medium with final concentration 1-5 μM bright yellow-green fluorescence was detected, associated with intracellular membrane structues and lipid drops. p-Diethylamino-BDI-BF2 showed high affinity to organic solvents and accumulated in cell membranes.

The cell staining was performed very fast during several seconds.

The cell staining of the cells, temporarily expressing chimer protein EGFP-XRCC (nuclear localization), was carried out by p-diethylamino-BDI-BF2 in concentration 5 μM to compare fluorescent properties of the compound p-diethylamino-BDI-BF2 to the green fluorescent protein EGFP. Photostability of p-diethylamino-BDI-BF2 was many times more than photostability of EGFP. Thus, during the half-life time of EGFP under the action of outer radiation, the actual decrease of fluorescence intensity of p-diethylamino-BDI-BF2 did not exceed 5-10%.

What is claimed is:

1. A compound of the formula (I):

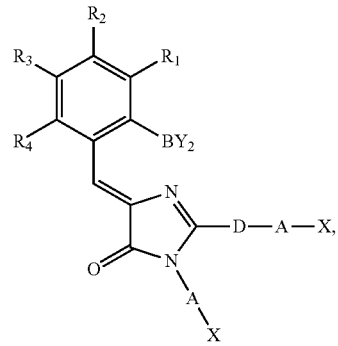

where
A is selected from linear or branched $C_{1-6}$ alkyl or $C_{4-6}$ cycloalkyl,
D is selected from aryl, heteroaryl, or may be absent,
X is selected from hydrogen, halogen, unsubstituted or $C_{1-6}$ alkyl substituted aminogroup, in which substituents not necessarily form cyclic substituted pyrrol or pyrrolidine derivatives, or $C_{4-6}$ cycloalkyl substituted aminogroup, azide, isothiocyanate, isocyanate, alcohol or thiol group, acethylene fragment, carboxyl group, or may be absent,
Y is independently selected from fluorine, hydroxyl or alkoxyl group with $C_{1-6}$ alkyl substituent,
$R_1$, $R_2$, $R_3$, $R_4$ are independently selected from hydrogen, halogen, unsubstituted or $C_{1-6}$ alkyl substituted aminogroup, in which substituents not necessarily form cyclic substituted pyrrol or pyrrolidine derivatives, or $C_{4-6}$ cycloalkyl substituted aminogroup, hydroxyl or $C_{1-6}$ alkyl alkoxyl group,
and also its salts and/or stereoisomers.

2. A compound according to claim 1, which is (Z)-4-(2-(-difluoroboryl)-4-hydroxybenzylidene)-1,2-dimethyl-1H-imidazole-5(4H)-one, for biomolecules' labeling.

3. A compound which is (Z)-4-(4-(diethylamino)-2-(difluoroboryl)benzylidene)-1,2-dimethyl-1H-imidazole-5 (4H)-one, for staining of cell membranes.

4. A compound according to claim 1, in which $R_2$ is OH, showing photoacidic properties.

5. A compound according to claim 4, which is (Z)-4-(2-(-difluoroboryl)-3,5-difluoro-4-hydroxybenzylidene)-1,2-dimethyl-1H-imidazole-5(4H)-one.

6. Fluorescent compounds selected from the group consisting of:
(Z)-4-(4-(diethylamino)-2-(difluoroboryl)benzylidene)-1-methyl-2-((E)-steryl)-1H-imidazole-5(4H)-one; and
(Z)-4-(2-(difluoroboryl)-4-hydroxybenzylidene)-2-(((E)-2-(dimethylamino)vynil)-1-methyl-1H-imidazole-5 (4H)-one;
for biomolecules labeling or staining of cell membranes.

* * * * *